United States Patent [19]

Somani et al.

[11] Patent Number: 5,846,521

[45] Date of Patent: Dec. 8, 1998

[54] PRESSURIZED SOLVENT-FREE DRUG AEROSOL COMPOSITIONS CONTAINING HYDROFLUOROCARBON PROPELLANTS

[75] Inventors: Asit Somani, Loughborough; Clive Booles, Shepshed, both of England

[73] Assignee: Fisons plc, Ipswich, England

[21] Appl. No.: 892,169

[22] Filed: Jul. 14, 1997

Related U.S. Application Data

[63] Continuation of Ser. No. 449,997, May 25, 1995, abandoned, which is a continuation of Ser. No. 280,301, Jul. 26, 1994, abandoned, which is a continuation of Ser. No. 965,382, filed as PCT/GB91/01023, Jun. 25, 1991, abandoned.

[30] Foreign Application Priority Data

| Jun. 29, 1990 | [GB] | United Kingdom | 9014526 |
| Jun. 29, 1990 | [GB] | United Kingdom | 9014527 |
| Nov. 3, 1990 | [GB] | United Kingdom | 9023953 |

[51] Int. Cl.⁶ ...................................... A61K 9/12
[52] U.S. Cl. .............................. 424/45; 424/46; 514/937; 514/975
[58] Field of Search ................................ 424/45, 47, 46; 514/958, 937, 975

[56] References Cited

U.S. PATENT DOCUMENTS

| 4,174,295 | 11/1979 | Bargigia et al. | 424/45 |
| 4,810,488 | 3/1989 | Jinks | 424/45 |
| 5,225,183 | 7/1993 | Purewal et al. | 424/45 |
| 5,605,674 | 2/1997 | Purewal et al. | 424/45 |
| 5,653,962 | 8/1997 | Akehurst et al. | 424/45 |
| 5,658,549 | 8/1997 | Akehurst et al. | 424/45 |

FOREIGN PATENT DOCUMENTS

| 0 379 793 | 1/1990 | European Pat. Off. . |
| 0379793 | 1/1990 | European Pat. Off. . |
| 0 384 371 | 2/1990 | European Pat. Off. . |
| 0384371 | 2/1990 | European Pat. Off. . |
| 0 372 777 | 6/1990 | European Pat. Off. . |
| 2 046 093 | 11/1980 | United Kingdom . |
| 90/11754 | 10/1980 | WIPO . |
| 88/07855 | 10/1988 | WIPO . |

*Primary Examiner*—Raj Bawa
*Attorney, Agent, or Firm*—Marshall, O'Toole, Gerstein, Murray & Borun

[57] ABSTRACT

Pressurised aerosol compositions comprise a medicament, a hydrofluorocarbon propellant and a polyethoxylated surfactant, the compositions containing substantially no solvent, other than the propellant, capable of increasing the solubility of the surfactant in the propellant. The compositions according to the invention are advantageous in that the solubility of the surfactant is such as to ensure good dispersion of the medicament and smooth operation of the aerosol valve.

14 Claims, No Drawings

PRESSURIZED SOLVENT-FREE DRUG AEROSOL COMPOSITIONS CONTAINING HYDROFLUOROCARBON PROPELLANTS

CROSS-REFERENCE TO RELATED APPLICATION

This application is a continuation of application Ser. No. 08/449,997, filed May 25, 1995, abandoned which is a continuation of application Ser. No. 08/280,301, filed Jul. 26, 1994, now abandoned, which is a continuation of application Ser. No. 07/965,382, filed as PCT/GB91/01023, Jun. 25, 1991, now abandoned.

This invention relates to pressurised aerosol compositions, in particular compositions of powdered inhalation medicaments.

Pressurised aerosols for the administration of medicaments, and indeed for other applications, conventionally contain one or more liquified chlorofluorocarbons (CFC's) as propellant. Such materials are suitable for use in such applications since they have the right vapour pressures (or can be mixed in the right proportions to achieve a vapour pressure in the right range) and are essentially taste- and odour-free.

In recent years there has been increasing concern about the depletion of the ozone layer in the upper atmosphere. This is believed to be due to the release into the atmosphere of CFC's and has led to a search for alternative agents for use in all applications of CFC's. To this end, aerosols for many applications are now pressurised using pressurised gases such as nitrogen or hydrocarbons. However, such propellants are generally not suitable for use in the administration of inhalation medicaments since they are toxic and/or the pressure within the canister falls each time the device is used which leads to unreproducible dosing.

The use of hydrofluorocarbons as aerosol propellants has also been suggested but this has the disadvantage that other excipients, in particular the surfactants generally used in aerosol formulations, such as sorbitan trioleate and oleic acid, are insufficiently soluble in these materials. Surfactants are required inter alia to ensure good dispersion of the powdered medicament and smooth operation of the valve through which the composition is dispensed.

European Patent Application 0 372 777 offers a solution to the problem of poor solvating properties of the hydrofluorocarbons by adding to the formulation a solvent, eg ethanol, capable of increasing the solubility of the surfactant in the propellant. This apparent solution suffers from the disadvantage that many of the solvents ("adjuvants") suggested are flammable, toxic and/or affect the stability and dispersion characteristics of the formulation.

Surprisingly, we have found a group of surfactants having a particular structural feature which are sufficiently soluble in hydrofluorocarbon propellants to permit the formulation of satisfactory pressurised aerosol formulations without the need for additional solvents.

Thus, according to the invention there is provided a pressurised aerosol composition comprising a medicament, a hydrofluorocarbon propellant and a polyethoxylated surfactant, the composition containing substantially no solvent, other than the propellant, capable of increasing the solubility of the surfactant in the propellant.

The compositions according to the invention are advantageous in that the solubility of the surfactant is such as to ensure good dispersion of the medicament and smooth operation of the aerosol valve. In addition, certain of the formulations disclosed herein are advantageous over prior art formulations in that they are more stable, are less toxic, have more suitable vapour pressures for the administration of medicaments by inhalation, more readily produced, perform better, eg in dispersion tests carried out using an impinger, or have other advantageous pharmaceutical properties.

The propellant mixtures of the present invention may also be advantageous in that they are substantially taste- and odour-free and have suitable vapour pressures for the administration of medicaments by inhalation, yet are environmentally safe and acceptable, especially when compared with compositions including chlorofluorocarbons. In addition, they may be less irritant than corresponding compositions including conventional surfactants such as oleic acid and sorbitan trioleate.

We prefer surfactants which have an average number, n, of from 2–50, more preferably 2–40, particularly 2–30, and especially 4–20, polyethoxylate units per molecule of surfactant.

Although the surfactant may consist completely of polyethoxylate units, ie is polyethylene glycol, eg having an average molecular weight of from 200 to 4000, we prefer surfactants in which the polyethoxylated portion is from 10–90%, more preferably 10–70%, particularly 10–50% by weight of the surfactant.

We prefer surfactants having an average molecular weight of less then 20,000, more preferably less than 10,000 and particularly less than 5000. We prefer surfactants having an average molecular weight greater than 200, more preferably 400 and especially 1000.

We prefer surfactants which are block copolymers of ethylene oxide and propylene oxide, particularly those polymers known as poloxamers. These surfactants have the general formula

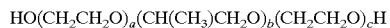

$$HO(CH_2CH_2O)_a(CH(CH_3)CH_2O)_b(CH_2CH_2O)_cH$$

in which a and c are generally in the range 2 to 130 and b is in the range 15 to 67; these compounds are block copolymers with the polyethoxylate portions accounting for between 20 and 90% by weight. These surfactants are available under the registered trademark Synperonic PE (ICI) and the registered trademark Pluronic (BASF). Particularly suitable poloxamers include the following Synperonic PE surfactants:

L35, L42, L44, L61, L62, L62F, L64, L75, L81, P85, L92 P94, L101 and L121;

in which L indicates that the surfactants are liquids, P that they are pastes, the first digit is a measure of the molecular weight of the polypropylene portion of the surfactant and the last digit of the number, multiplied by 10, gives the per cent ethylene oxide content of the surfactant. Further characterising details of these surfactants, and the majority of surfactants described herein, are given in Surfactants Europa, 2nd Edition, 1989, compiled and edited by Gordon L Hollis and published by Tergo-Data, the entire contents of which are hereby incorporated by reference.

Other suitable poloxamers include the following Pluronic PE surfactants:

3100, 4300, 6100, 6200, 6400, 8100 and 9200.

We prefer poloxamers which contain less than 60% by weight of ethylene oxide.

We also prefer block copolymers of ethylene oxide in which a polyethylene glycol moiety has been used as the initiator molecule for the polymerisation, giving compounds of the general formula:

HO(CH(CH$_3$)CH$_2$O)$_x$(CH$_2$CH$_2$O)$_y$(CH(CH$_3$)CH$_2$O)$_z$H which typically have a molecular weight of the order of 3000 with the ethylene oxide portions accounting for typically 10–20% by weight; these compounds are available under the tradename Synperonic RPE (ICI) and Pluronic RPE (BASF). Especially preferred surfactants include Pluronic RPE2510, RPE2520 and RPE3110.

We prefer surfactants having a hydrophobic portion derived from an alkylphenol, an alcohol or ethylenediamine.

Particular surfactants derived from an alkylphenol that may be mentioned include a) compounds of the general formula

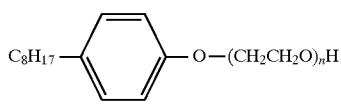

in which n represents the average number of ethoxylate groups per molecule; these compounds are available under the registered trademark Synperonic OP (ICI), and b) compounds of the general formula

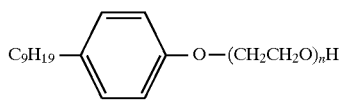

in which n represents the mean number of ethoxylate groups per molecule; these compounds are available under the tradename Synperonic NP (ICI). Suitable examples of these surfactants include the following Synperonic surfactants:

NP4, NP5, NP6, NP7, NP8, NP9, NP10, NP12, NP15, OP10 and OP11.

Alcohol derived surfactants may be derived from a monohydric or polyhydric alcohol. Particular mono-hydric alcohols that may be mentioned include straight or branched chain C$_8$ to C$_{20}$ alcohols. Suitable surfactants that may be mentioned include the alcohol ethoxylates available under the tradename Synperonic LF (ICI).

Polyhydric alcohols from which the surfactant may be derived include glycerol and sorbitan. The polyhydric alcohol may be partially esterified, eg, with a fatty carboxylic acid, such as lauric, palmitic and especially oleic acid. We particularly prefer surfactants which are polyethoxylated derivatives of sorbitan mono-oleate, for example, polysorbate 20, 40, 60 and 80.

Surfactants having a portion derived from ethylenediamine that may be particularly mentioned include the Synperonic T series of compounds (ICI) of general formula

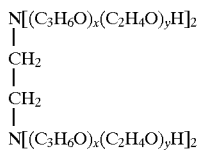

in which x and y are in the ranges 4–25 and 1–120 respectively. Particular examples of these surfactants that may be specifically mentioned include Synperonic T701, T304 and T702.

In the present context, the term 'hydrofluorocarbon' is to be taken to mean a compound of general formula C$_x$H$_y$F$_z$ in which x is an integer from 1 to 3, y+z=2x+2 and y and z are both at least 1.

Particular hydrofluorocarbons of interest are CF$_3$CFH$_2$ (Propellant 134a), CH$_3$CHF$_2$ (Propellant 152a) and CF$_3$CHFCF$_3$ (Propellant 227). We particularly prefer formulations containing Propellant 227.

In general the vapour pressure of the mixture should be in the range suitable and permitted for aerosol propellants. The vapour pressure may be varied by mixing one or more hydrofluorocarbons and/or some other suitable vapour pressure modifying agent in appropriate proportions.

We prefer the vapour pressure of the mixture to be in the range 20 to 100 psi, more preferably 40 to 80 psi, eg about 60 psi.

The amount of surfactant in the composition will generally be from about 0.01 to 10% by weight, more preferably from about 0.1 to 5%, eg about 1%.

The properties of the invention, notably the absence of any co-solvent for the surfactant, render it particularly useful in the pharmaceutical field.

The medicament may be in solid, particulate form (ie the composition may be a suspension), or the active ingredient may be dissolved in the propellant.

Medicaments which may be dispersed in the composition according to the invention include any medicaments which are conventionally administered by inhalation of a pressurised aerosol formulation. Such medicaments include drugs for use in the prophylactic or remedial treatment of reversible obstructive airways disease, eg drugs such as sodium cromoglycate, nedocromil sodium, inhaled steroids such as beclomethasone dipropionate, tipredane, fluticasone, anticholinergic agents such as ipratropium bromide, and bronchodilators, eg salmeterol, salbutamol, reproterol, terbutaline, fenoterol and salts thereof. We find that the formulations are particularly advantageous for formulating salts of carboxylic acids, particularly dicarboxylic acids such as nedocromil and cromoglycic acid.

Where the medicament is solid, it preferably has a particle size distribution such that a high, proportion of the particles are of a size capable of penetrating deep into the lung. In particular, the active ingredient is preferably in a form having a mass median diameter of from 0.1 to 10 $\mu$m, more preferably from 0.1 to 4 $\mu$m, eg about 2 or 3$\mu$m.

We prefer the active ingredient to have a mass median diameter in the range 0.01 to 10 microns, more preferably from 1 to 5 microns. The composition preferably comprises from 0.05 to 15, preferably from 0.1 to 10, and most preferably from 0.5 to 5% w/w of the active ingredient.

In producing the compositions according to the invention, a container equipped with a valve is filled with a propellant containing the finely-divided medicament. The container may first be charged with a weighed amount of medicament which has been ground to a predetermined particle size, or with a slurry of powder in the cooled liquid propellant. The container may alternatively be filled by introducing powder and propellant by the normal cold filling method, or a slurry of the powder in one component of the propellant may be placed in the container, the valve sealed in place, and the balance of the propellant then introduced by pressure filling through the valve nozzle. As a further alternative a bulk quantity of the total composition may be filled into the container through the valve.

The invention is illustrated by the following example:

EXAMPLE

Compositions were prepared by cold filling of the ingredients into aluminium aerosol cannisters which were then sealed by crimping a 50 $\mu$l or 100 $\mu$l aerosol valve in place.

The following combinations of micronised active ingredient, surfactant and propellant were used:

| | | |
|---|---|---|
| 1. Nedocromil sodium | 0.2000 g | |
| Synperonic PEL 62 | 0.0612 g | |
| HFC 134a | 11.9788 g | |
| 2. Nedocromil sodium | 0.2000 g | |
| Pluronic PE 6200 | 0.0612 g | |
| HFC 134a | 11.9788 g | |
| 3. Nedocromil sodium | 0.2000 g | |
| Synperonic NP 15 | 0.0612 g | |
| HFC 134a | 11.9788 g | |
| 4. Nedocromil sodium | 0.2000 g | |
| Synperonic PEL 62 | 0.0706 g | |
| HFC 227 | 13.8494 g | |
| 5. Nedocromil sodium | 0.2000 g | |
| Pluronic PE 6200 | 0.0706 g | |
| HFC 227 | 13.8494 g | |
| 6. Nedocromil sodium | 0.2000 g | |
| Synperonic NP 15 | 0.0706 g | |
| HFC 227 | 13.8494 g | |
| 7. Sodium cromoglycate | 0.5000 g | |
| Synperonic PEL 62 | 0.0612 g | |
| HFC 134a | 11.6788 g | |
| 8. Sodium cromoglycate | 0.5000 g | |
| Pluronic PE 6200 | 0.0612 g | |
| HFC 134a | 11.6788 g | |
| 9. Sodium cromoglycate | 0.5000 g | |
| Synperonic NP 15 | 0.0612 g | |
| HFC 134a | 11.6788 g | |
| 10. Sodium cromoglycate | 0.5000 g | |
| Synperonic PEL 62 | 0.0706 g | |
| HFC 227 | 13.5494 g | |
| 11. Sodium cromoglycate | 0.5000 g | |
| Pluronic PE 6200 | 0.0706 g | |
| HFC 227 | 13.5494 g | |
| 12. Sodium cromoglycate | 0.5000 g | |
| Synperonic NP 15 | 0.0706 g | |
| HFC 227 | 13.5494 g | |
| 13. Nedocromil sodium | 0.2000 g | |
| Polyethylene glycol PEG 200 | 0.0706 g | |
| HFC 227 | 13.8494 g | |
| 14. Nedocromil sodium | 0.2000 g | |
| Polyethylene glycol PEG 600 | 0.0706 g | |
| HFC 227 | 13.8494 g | |
| 15. Nedocromil sodium | 0.2000 g | |
| Polysorbate 80 | 0.0706 g | |
| HFC 227 | 13.8494 g | |
| 16. Nedocromil sodium | 0.2000 g | |
| Polysorbate 20 | 0.0706 g | |
| HFC 227 | 13.8494 g | |
| 17. Nedocromil sodium | 0.2000 g | |
| Polysorbate 80 | 0.0122 g | |
| HFC 134a | 12.0278 g | |
| 18. Nedocromil sodium | 0.2000 g | |
| Synperonic PEP 85 | 0.0122 g | |
| HFC 134a | 12.0278 g | |

In all cases stable suspensions of the active ingredient in the propellant were obtained.

We claim:

1. A pressurized aerosol composition consisting essentially of
   a medicament in an amount up to 15% by weight of the composition;
   a hydrofluorocarbon propellant; and
   a surfactant having a molecular weight less than 20,000 which is selected from the group consisting of polyethylene glycol, a block copolymer of ethylene oxide and propylene oxide, and a polyethoxylated surfactant having a hydrophobic portion derived from an alkyl phenol, a monohydric alcohol, a polyhydric alcohol which can be partially esterified, or ethylene diamine;
   said composition containing about 0.01% to 10% by weight of said surfactant;
   the vapor pressure of said composition being in the range of 20–100 psi; and
   the composition being free from any solvent, other than the propellant, which increases the solubility of the surfactant in the propellant.

2. A composition in accordance with claim 1 wherein said surfactant is selected from the group consisting of
   (a) polyethylene glycol;
   (b) block copolymers of ethylene oxide and propylene oxide having the general formula $HO(CH_2CH_2O)_a(CH(CH_3)CH_2O)_b(CH_2CH_3O)_cH$ 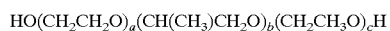

in which a and c are integers in the range of 2 to 130 and b is an integer in the range of 15 to 67;

(c) block copolymers of ethylene oxide in which a polyethylene glycol moiety has been used as the initiator molecule for the polymerization, giving compounds of the general formula $HO(CH(CH_3)CH_2O)_x(CH_2CH_2O)_{y(CH(CH3)}CH_2O)_zH;$ 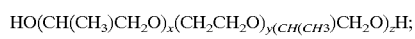

(d) surfactants derived from an alkylphenol of the general formula

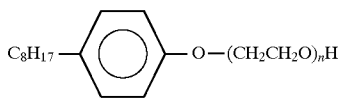

in which n represents the average number of ethoxylate groups per molecule;

(e) surfactants derived from an alkylphenol of the general formula

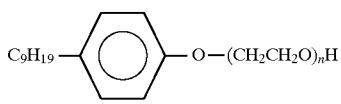

in which n represents the mean number of ethoxylate groups per molecule;

(f) surfactants derived from a monohydric alcohol of the general formula $RO(CH_2CH_2O)_nH$ 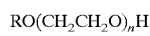

in which R represents a straight or branched chain $C_8$ to $C_{20}$ alkyl group;

(g) surfactants derived from a polyhydric alcohol of the formula

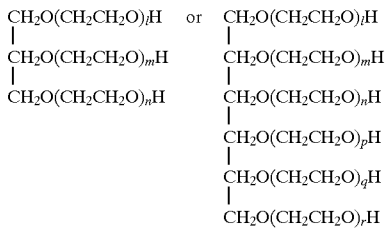

or a cyclized anhydride thereof, which can be partially esterified; and (h) surfactants having a portion derived from ethylenediamine of general formula

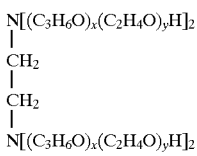

in which x and y are in the ranges 4–25 and 1–120 respectively.

3. A pressurized aerosol composition consisting essentially of a medicament in an amount up to 15% by weight of the composition;

a hydrofluorocarbon propellant selected from the group consisting of (1,1,1,2)-tetrafluoroethane, (1,1,1,2,3,3,3)-heptafluoropropane, and mixtures thereof; and a surfactant having a molecular weight less than 20,000 which is selected from the group consisting of polyethylene glycol, a block copolymer of ethylene oxide and propylene oxide, and a polyethoxylated surfactant having a hydrophobic portion derived from an alkyl phenol, a monohydric alcohol, a polyhydric alcohol which can be partially esterified, or ethylene diamine;

said composition containing about 0.01% to 10% by weight of said surfactant;

the vapor pressure of said composition being in the range of 20–100 psi; and the composition being free from any solvent, other than the propellant, which increases the solubility of the surfactant in the propellant.

4. The composition of claim 3 wherein the hydrofluorocarbon propellant is 1,1,1,2,3,3,3-heptafluoropropane.

5. The composition of claim 3 wherein the surfactant is present in the composition in an amount of about 0.1% to 5% by weight.

6. A composition according to claim 1, wherein the surfactant has an average number of from 2–50 polyethoxylate units per molecule of surfactant.

7. A composition according to claim 1, wherein the surfactant is a block copolymer of ethylene oxide and propylene oxide.

8. A composition according to claim 1, wherein the surfactant has a hydrophobic portion derived from the group consisting of alkylphenol, an alcohol and ethylenediamine.

9. A composition according to claim 8, wherein the alcohol is a monohydric alcohol.

10. A composition according to claim 8, wherein the alcohol is polyhydric.

11. A composition according to claim 10, wherein the polyhydric alcohol is partially esterified.

12. A composition according to claim 1, wherein the surfactant is polysorbate 20, polysorbate 40, polysorbate 60 or polysorbate 80.

13. A composition according to claim 1, wherein the propellant is selected from (1,1,1,2)-tetrafluoroethane, (1,1)-difluoroethane, and (1,1,1,2,3,3,3,)-heptafluoropropane.

14. A composition according to claim 1, wherein the propellant is propellant 227.

* * * * *

UNITED STATES PATENT AND TRADEMARK OFFICE
CERTIFICATE OF CORRECTION

PATENT NO. : 5,846,521
DATED : December 8, 1998
INVENTOR(S) : Asit Somani et al.

It is certified that error appears in the above-identified patent and that said Letters Patent is hereby corrected as shown below:

Column 4, after line 20, insert the following paragraph:

--The compositions according to the invention may be used in a wide variety of fields, with the active ingredient being chosen appropriately, but the properties of the invention, notably the absence of any co-solvent for the surfactant, render it particularly useful in the pharmaceutical field.--

Column 4, line 38, "high, proportion" should be --high proportion--

Column 6, line 20, "$HO(CH(CH_3)CH_2O)_x(CH_2CH_2O)_{y(CH(CH3)}CH_2O)_zH$" should be --$HO(CH(CH_3)CH_2O)_x(CH_2CH_2O)_y(CH(CH_3)CH_2O)_zH$--

Signed and Sealed this

Eighteenth Day of April, 2000

Attest:

Q. TODD DICKINSON

*Attesting Officer*       *Director of Patents and Trademarks*